United States Patent [19]
Peel et al.

[11] 3,952,019
[45] Apr. 20, 1976

[54] BICYCLO-OCTANE DERIVATIVES
[75] Inventors: Richard Philip Peel; James Kenneth Sutherland, both of Manchester, England
[73] Assignee: Imperial Chemical Industries Limited, London, England
[22] Filed: Apr. 30, 1974
[21] Appl. No.: 465,557

[30] Foreign Application Priority Data
May 15, 1973 United Kingdom............... 23045/73

[52] U.S. Cl...................... 260/343.2 R; 260/347.3; 260/468 R; 260/468 D; 260/476 R; 260/488 F; 260/488 B; 260/514 D; 260/514 G; 260/343.3 R
[51] Int. Cl.²...................... C07D 311/92
[58] Field of Search................... 260/343.2

[56] References Cited
UNITED STATES PATENTS
3,892,733    7/1975    Brown............................ 260/240 R Primary Examiner—James A. Patten
Attorney, Agent, or Firm—Cushman, Darby & Cushman

[57] ABSTRACT

The disclosure relates to a series of novel prostaglandin intermediates, the preparation of which in sequence constitutes a novel process for the manufacture of known diol intermediates, for example 2,3,3a-$\beta$,6a$\beta$-tetrahydro-5$\alpha$-hydroxy-4$\beta$-(3-hydroxyoct-1-trans-enyl)-2-oxocyclopenteno[b]furan, from the readily available norbornadiene, said process comprising fewer and more easily operable stages than previously known processes for the manufacture of said diol intermediates.

3 Claims, No Drawings

BICYCLO-OCTANE DERIVATIVES

This invention relates to novel intermediates which are useful for the manufacture of prostaglandins and prostaglandin-like compounds.

According to the invention there is provided 3-oxotricyclo[2,2,1,0$^{2,6}$]heptane-5 -anti*-carboxylic acid (I).

According to a further feature of the invention there is provided a process for the manufacture of 3-oxo-tricyclo[2,2,1,0$^{2,6}$]heptane-5-anti-carboxylic acid which comprises the oxidation of 3-formyloxy-5-anti-(formyloxymethyl)-tricyclo[2,2,1,0$^{2,6}$]heptane (II) with, for example, Jones' reagent (chromic acid in acetone).

The 3-formyloxy-5-anti-(formyloxymethyl)tricyclo[2,2,1,0$^{2,6}$]heptane used as starting material in the above process may be manufactured by reaction of norbornadiene (III) with formaldehyde in formic acid (the Prins reaction) to give II together with a minor amount of the corresponding 5-syn*-(formyloxymetyl) compound.

*anti refers to a substituent on the opposite side of the bridgehead to the 3-oxygen function, and syn refers to a substituent on the same side of the bridgehead as the 3-oxygen substituent

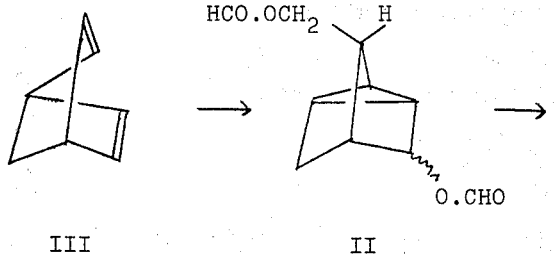

According to a further feature of the invention is provided a ketone of the formla:-

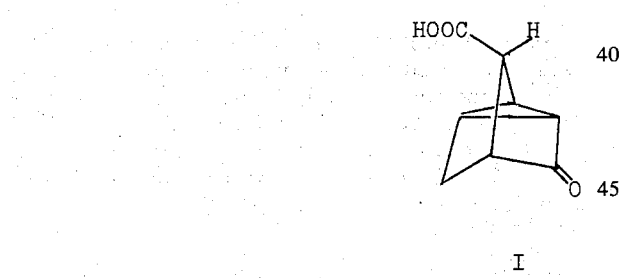

wherein R$^1$ is a bromine, chlorine or iodine atom or an alkanoyloxy radical of 1 to 6 carbon atoms.

A suitable value for R$^1$ when it is an alkanoyloxy radical is, for example, an acetoxy radical.

According to a further feature of the invention there is provided a process for the manufacture of a ketone IV which comprises, for those ketones wherein R$^1$ is a bromine, chlorine or iodine atom, the reaction of a 3-oxotricyclo[2,2,1,0$^{2,6}$]heptane-5-carboxylic acid with, respectively, a hydrobrominating, hydrochlorinating or hydroiodinating agent, for example hydrogen bromide/acetic acid or concentrated hydrochloric acid, or, for those ketones wherein R$^1$ is an alkanoyloxy radical of 1 to 6 carbon atoms, with a mixture of an alkanoic acid of 1 to 6 carbon atoms for example acetic acid and perchloric acid.

The 3-oxotricyclo[2,2,1,0$^{2,6}$]heptane-5-syn-carboxylic acid which may be used as a starting material in the above process is a known compound.

According to a further feature of the invention there is provided a lactone of the formula:-

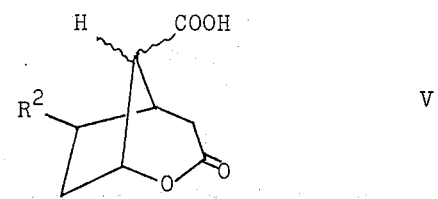

wherein R$^2$ is a hydrogen, bromine, chlorine or iodine atom or an alkanoyloxy radical of 1 to 6 carbon atoms, for example an acetoxy radical.

According to a further feature of the invention there is provided a process for the manufacture of a lactone of the formula V which comprises the oxidation, for example with peracetic acid, of a ketone of the formula IV whereafter when a lactone is required wherein R$^2$ is a hydrogen atom, the corresponding lactone wherein R$^2$ is a bromine, chlorine or iodine atom is hydrogenolysed, for example with zinc and acetic acid.

According to a further feature of the invention there is provided a lactone of the formula:

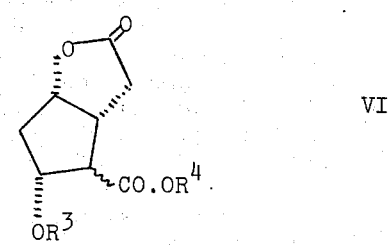

wherein R$^3$ is a hydrogen atom or an aroyl radical of up to 12 carbon atoms, for example a 4-phenylbenzoyl radical, and R$^4$ is a hydrogen atom, an alkyl radical of 1 to 6 carbon atoms, for example a methyl radical, or a phenacyl radical, optionally substituted in the phenyl part thereof by halogen or alkyl or alkoxy of 1 to 6 carbon atoms, for example a 4-bromophenacyl radical.

Particular lactones of the invention of the formula VI are 2,3,3a$\beta$,6a$\beta$-tetrahydro-5$\alpha$-hydroxy-2-oxocyclopenteno[b]-furan-4$\beta$-carboxylic acid, methyl 2,3,3a$\beta$,6a$\beta$-tetrahydro-5$\alpha$-hydroxy-2-oxocyclopenteno[b]furan-4$\beta$-carboxylate, 4-bromophenacyl 2,3,3a$\beta$,6a$\beta$-tetrahydro-5$\alpha$-hydroxy-2-oxocyclopenteno-[b]furan-4$\beta$-carboxylate, methyl 2,3,3a$\beta$,6a$\beta$-tetrahydro-2-oxo-5$\alpha$-(4-phenylbenzoyloxy)cyclopenteno[b]furan-4$\beta$-carboxylate, 4-bromophenacyl 2,3,3a$\beta$,6a$\beta$-tetrahydro-2-oxo-5$\alpha$-(4-phenylbenzoyloxy)cyclopenteno[b]furan-4$\beta$-carboxylate or 2,3,3a$\beta$,6a$\beta$-tetrahydro-2-oxo-5$\alpha$-(4-phenylbenzoyloxy)cy-

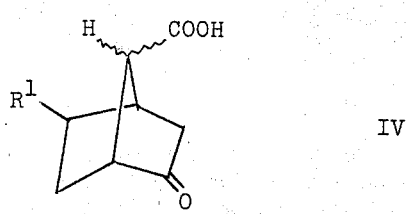

clopenteno[b]furan-4β-carboxylic acid.

According to a further feature of the invention there is provided a process for the manufacture of a lactone of the formula VI which comprises:

a. for those lactones wherein $R^3$ and $R^4$ are both hydrogen atoms, the reaction of a lactone of the formula V wherein $R^1$ is a bromine, chlorine or iodine atom, with hydroxylamine in the presence of a tertiary organic base, for example a collidine;

b. for those lactones wherein $R^3$ and $R^4$ are both hydrogen atoms, the reaction of an acid of the formula:

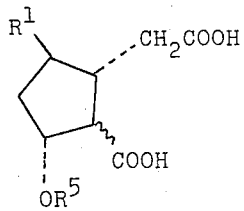

VII wherein $R^1$ is a bromine, chlorine or iodine atom, and $R^5$ is an alkanoyl radical of 1 to 6 carbon atoms, for example an acetyl radical, with a base, for example sodium hydroxide;

c. for those lactones wherein $R^3$ is a hydrogen atom and $R^4$ is a phenacyl radical, the reaction of the corresponding lactone wherein $R^3$ and $R^4$ are both hydrogen atoms, with a phenacyl halide, for example a phenacyl bromide;

d. for those lactones wherein $R^3$ is an aroyl radical and $R^4$ is a phenacyl radical, the reaction of the corresponding lactone wherein $R^3$ is a hydrogen atom and $R^4$ is a phenacyl radical with an aroyl halide, for example an aroyl chloride;

e. for those lactones wherein $R^3$ is an aroyl radical and $R^4$ is a hydrogen atom, the selective deprotection of the corresponding lactone wherein $R^3$ is an aroyl radical and $R^4$ is a phenacyl radical, with, for example, zinc and acetic acid;

f. for those lactones wherein $R^3$ is an aroyl radical and $R^4$ is a hydrogen atom, the reaction of a corresponding lactone wherein $R^3$ and $R^4$ are both a hydrogen atom, with an aroyl halide, for example an aroyl chloride; or g. for those lactones wherein $R^3$ is an aroyl radical and $R^4$ is an alkyl radical, the cyclisation, for example with silver acetate in acetic acid, of a compound of the formula:

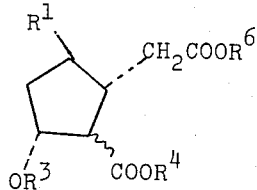

VIII wherein $R^1$ is a bromine, chlorine or iodine atom, $R^3$ is an aroyl radical and $R^4$ and $R^6$ are each an alkyl radical of 1 to 6 carbon atoms.

The starting material of the formula VII used in the above process may be obtained by acid hydrolysis of a lactone of the formula V in the presence of an alkanoic acid, $R^5OH$, for example by hydrolysis with hydrogen bromide/acetic acid.

The starting material of the formula VIII used in the above process may be obtained by treatment of a lactone V ($R^2$ = bromine, chlorine or iodine) with an alkanol of 1 to 6 carbon atoms, for example methanol, and a strong acid, for example sulphuric acid, to give a bis-ester IX, which is esterified with an aroyl halide, for example an aroyl chloride, to give the required compound VIII.

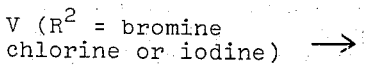

According to a further feature of the invention there is provided a process for the manufacture of the known prostaglandin intermediate:

X (PB = 4-phenylbenzoyl)

or the 4α-hydroxymethyl epimer thereof, which comprises the selective reduction, for example with diborane, of the corresponding lactone of the formula VI ($R^3$ = 4-phenylbenzoyl, $R^4$ = hydrogen).

According to a further feature of the invention there is provided a process for the manufacture of the known prostaglandin intermediate:

XI (PB = 4-phenylbenzoyl)

or the 4α-formyl epimer thereof, which comprises the reduction, for example with hydrogen and a palladium on barium sulphate catalyst, of the acid chloride of the corresponding acid of the formula VI ($R^3$ = 4-phenylbenzoyl, $R^4$ = hydrogen).

The said acid chloride may be prepared, for example, by reacting the acid with oxalyl chloride.

The compounds X and XI wherein the 4-substituent is in the α-configuration may be transformed to prostaglandins and prostaglandin-like compounds of the 12-epi series in exactly the same way as it is known to transform the 4β compounds X and XI to prostaglandins and prostaglandin-like compounds of the 12-natural series.

The novel lactones of the invention of the formula V may also be readily converted into prostaglandins or prostaglandin-like compounds of the 9-desoxy series (starting from compounds V wherein R¹ is hydrogen) the 9-epi series (starting from compounds V wherein R² is alkanoyloxy and the carboxyl group is anti) or 9,12-bis-epi series, which is the same as the 8,11-bis-epi series, (starting from compounds V wherein R² is alkanoyloxy and the carboxy group is syn) by conventional transformations which are well-known to the skilled organic chemist. For example, the transformation of a compound V to a prostaglandin or prostaglandin-like compound may be achieved by the following steps:

1. Conversion of the carboxy radical to a formyl radical, either directly by selective reduction, or by reduction to the corresponding hydroxymethyl compound, for example with diborane, and oxidation of hydroxymethyl to formyl, for example with chromic acid.

2. Reaction of the formyl group with a phosphonate reagent $(CH_3O)_2PO.CH_2.COR^7$, wherein $R^7$ is C-16 onwards of a known prostaglandin or prostaglandin-like compound, in the presence of a strong base to give an enone.

3. Reduction of the enone to the corresponding enol to give the "bottom" side chain $-CH\overset{\pm}{=}CH.CHOH.R^7$ of a known prostaglandin or prostaglandin-like compound.

4. Reduction of the lactone ring to a lactol with diisobutyl aluminium hydride.

5. Reaction of the lactol group with (4-carboxybutyl)triphenylphosphonium bromide and a strong base to give the 6-carboxy-1-cis-hexenyl "top" chain of a prostaglandin or a prostaglandin-like compound.

6. Removal of any hydroxy-protecting groups.

It will be understood, of course, that the steps may be carried out in different orders, provided that step 2 must follow step 1, step 3 must follow step 2, step 5 must follow step 4, and step 6 must be last. It will also be appreciated by the skilled organic chemist that, if the order of the steps is altered, it may be necessary to protect certain reactive substituents in the starting material for a particular reaction, and subsequently to remove the protecting group after completion of the reaction.

Prostaglandins and prostaglandin-like compounds of the C and 11-desoxy series may also be obtained, by Baeyer-Villiger oxidation of a 3-oxotricyclo[2,2,1,0²,⁶]heptane-5-carboxylic acid (I or syn-epimer) to a tricyclic lactone XII which on acid treatment, for example with hydrogen bromide in acetic acid, rearranges and eliminates to give the unsaturated derivative XIII. This unsaturated derivative XIII is lactonised and hydrogenated to give XIV (COOH = α) which is equilibrated with base to XIV (COOH = β) and the carboxy group is selectively reduced, for example with diborane, to give a hydroxymethyl compound which may be converted by conventional transformations, analogous to those described above, to prostaglandins and prostaglandin-like compounds of the 11-desoxy series. Alternatively, the hydrogenation step may be omitted, in order to give in a similar manner prostaglandins or prostaglandin-like compounds of the C-series. If the equilibration of XIV (COOH = α) to XIV (COOH = β) is omitted, compounds of the 11-desoxy-12-epi-series may be obtained.

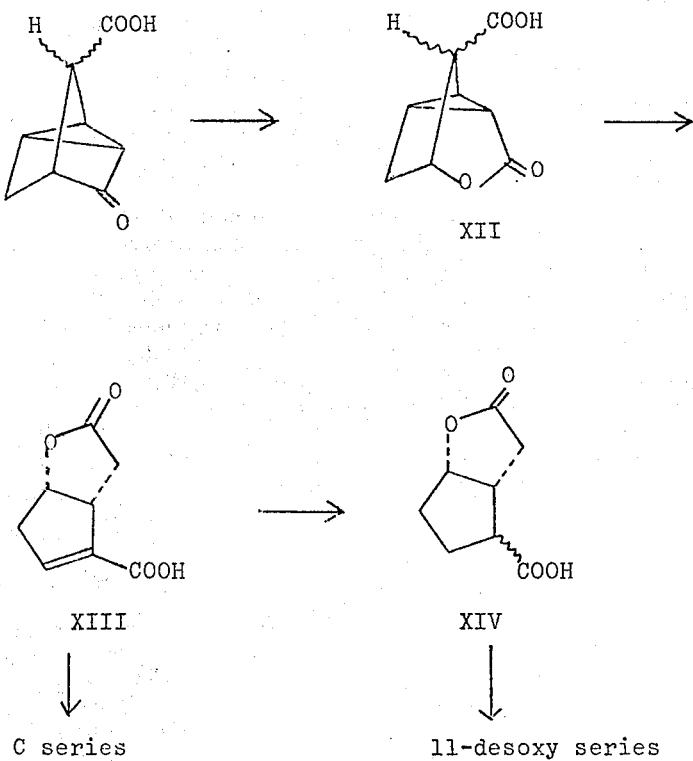

According to a further feature of the invention there is provided a lactone-aldehyde of the formula:

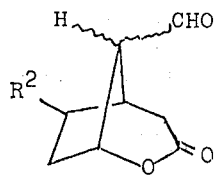

XV wherein $R^2$ has the meaning stated above.

A preferred compound of the formula XV is 6-exo-chloro-3-oxo-2-oxabicyclo[3,2,1]octane-8-anti-carbaldehyde.

According to a further feature there is provided a process for the manufacture of a lactone-aldehyde XV which comprises the oxidation, for example with Collins' reagent (chromium trioxide/pyridine) of the corresponding 8-hydroxymethyl compound.

The corresponding 8-anti-hydroxymethyl compound is a known compound, and the corresponding 8-syn-hydroxymethyl compound may be prepared by similar methods.

According to a further feature of the invention there is provided an enone-lactone of the formula:

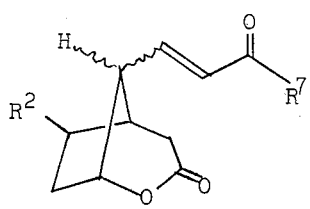

XVI wherein $R^2$ and $R^7$ have the meanings defined above.

A particular enone-lactone of the formula VI is 6-exo-chloro-3-oxo-8-anti-(3-oxo-oct-1-trans-enyl)-2-oxabicyclo-[3,2,1]octane.

According to a further feature of the invention there is provided a process for the manufacture of an enone-lactone of the formula XVI which comprises the reaction of a lactone-aldehyde of the formula XV with a phosphonate $(R^8O)_2PO.CH_2COR^7$ or a phosphorane $Ph_3P{:}CHCOR^7$, wherein $R^7$ has the meaning stated above and $R^8$ is an alkyl radical of 1 to 6 carbon atoms, for example a methyl or ethyl radical, in the presence of a strong base.

According to a further feature of the invention there is provided an enol-lactone of the formula:

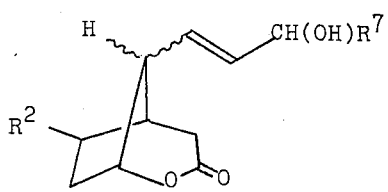

XVII wherein $R^2$ and $R^7$ have the meanings stated above.

A particular enol-lactone of the formula XVII is 6-exo-chloro-8-anti-(3-hydroxyoct-1-trans-enyl)-3-oxo-2-oxabicyclo[3,2,1]octane.

According to a further feature of the invention there is provided a process for the manufacture of an enol-lactone XVII which comprises the reduction of a corresponding enone-lactone XVI, for example with sodium borohydride, zinc borohydride, aluminium tri-isopropoxide or di-isobornyloxy aluminium isopropoxide.

According to a further feature of the invention there is provided a process for the manufacture of a known prostaglandin intermediate of the formula:

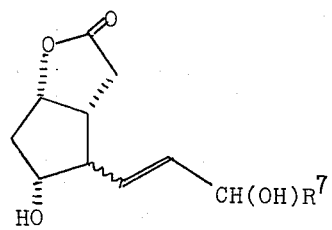

XVIII wherein $R^7$ has the meaning stated above, which comprises:

a. the rearrangement of an enol-lactone XVII, under basic conditions, for example with sodium hydroxide and hydrogen peroxide, or with hydroxylamine; or b. the reduction of an epoxy-ketone of the formula:

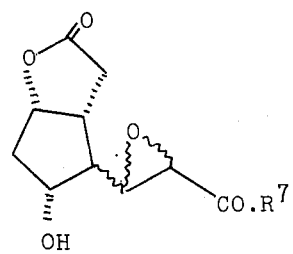

XIX wherein $R^7$ has the meaning stated above, for example with potassium iodide and acetic acid.

The epoxy-ketone XIX may be prepared, for example, by the reaction of an enone-lactone XVI with a strong base, for example sodium hydroxide, and hydrogen peroxide.

An alternative sequence of reactions for converting a lactone V to an enone XVI comprises reacting the acid chloride of V, prepared as described above, with an acetylene $HC \equiv CR^7$ in the presence of a Lewis acid, for example stannic chloride, to give an enone XX, which is reduced, for example with sodium borohydride, to an enol XXI, reaction of which with acid gives the required enone XVI.

It is to be understood that the invention relates both to the enantiomer shown in formula I, which is an intermediate for optically active prostaglandins of the natural series and analogous optically active prostaglandin-like compounds and also to the racemic form, comprising the enantiomer of the formula I and its mirror image, which racemic form is an intermediate for racemic prostaglandins and prostaglandin-like compounds, it being a matter of common general knowledge how the racemate may be resolved.

diluted with ether and filtered through Celite (trade mark) to remove paraformaldehyde. The filtrate was washed successively with water, twice with sodium bicarbonate solution and again with water, and was dried. The solvent was evaporated to give a golden yellow liquid which was distilled, the fraction b.p. 92°–102°C./0.05 mm. Hg. pressure being the diformyl compound, 3-formyloxy-5-anti-(formyloxymethyl)-tricyclo[2,2,1,0$^{2,6}$]heptane.

EXAMPLE 2

3-Oxotricyclo[2,2,1,0$^{2,6}$]heptane-5-anti-carboxylic

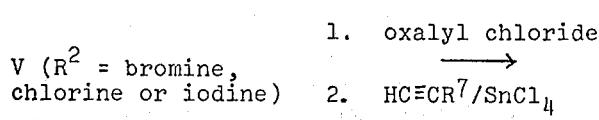

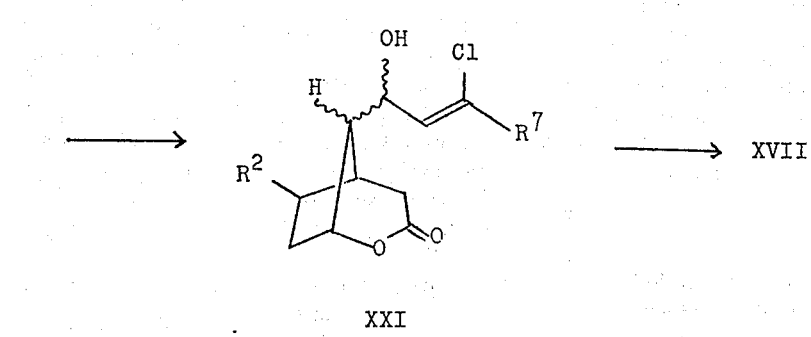

The invention is illustrated, but not limited, by the following Examples:

EXAMPLE 1

A solution of 3-formyloxy-5-anti-(formyloxymethyl)-tricyclo[2,2,1,0$^{2,6}$]heptane (10.28 g.) in acetone (100 ml.) was stirred and ice-cooled while Jones' reagent was added dropwise below 25°C. until thin-layer chromatography indicated the absence of the starting diformyl compound, about 4 hours. A solution of sodium pyrosulphite was added to destroy the excess of oxidising agent, the acetone was evaporated under reduced pressure, and the residue was extracted 4 times with ethyl acetate. The extracts were combined and dried, and the solvent was evaporated to give a solid, which was crystallised from a mixture of acetone and petroleum ether (b.p. 60°–80°C.) to give the ketoacid, 3-oxotricyclo[2,2,1,0$^{2,6}$]heptane-5-anti-carboxylic acid, m.p. 146°–147.5°C.

The 3-formyloxy-5-anti-(formyloxymethyl)tricyclo[2,2,1,0$^{2,6}$]heptane used as starting material in the above process may be prepared as follows:

A suspension of paraformaldehyde (60 g.) in 98–100% formic acid (900 ml.) was stirred vigorously and cooled while norbornadiene (60 g.) was added dropwise. After completion of the addition, the cooling was removed and the mixture was stirred at room temperature for 12 to 15 hours. The formic acid was evaporated under reduced pressure, and the residue was acid (6.86 g.) was dissolved in glacial acetic acid by warming, and to the solution was added 45% hydrogen bromide in acetic acid (20 ml.) in one portion. The reaction mixture was kept at 35°–40°C. until thin-layer chromatography on the system described above indicated the disappearance of the starting keto-acid — about 2 hours. The reaction mixture was poured into ice-water and extracted 4 times with ethyl acetate. The combined extracts were washed with water and dried, and the solvent was evaporated, last traces being removed by codistillation with toluene, to give 5-exo-bromo-2-oxobicyclo-[2,2,1]heptane-7-anti-carboxylic acid. This material is suitable for use as the starting material in the process of Example 6, but may if desired be crystallised from a mixture of acetone and petroleum ether (b.p. 60°–80°C.) to give material of m.p. 183.5° – 185.5°C.

EXAMPLE 3

A mixture of 3-oxotricyclo[2,2,1,0$^{2,6}$]heptane-5-anti-carboxylic acid (4.78 g.), concentrated hydrochloric acid (15 ml.) and glacial acetic acid (15 ml.) was heated for 1½ hours in an oil-bath a 120°C. The solution was cooled, poured into water and extracted three times with ethyl acetate. The extracts were combined, washed with brine and dried, and the solvent was evaporated under reduced pressure to give a crystalline residue. Crystallization of the residue from benzene/light petroleum gave 5-exo-chloro-2-oxobicyclo[2,2,1]-heptane-7-anti-carboxylic acid, m.p. 157.5°–160°C.

EXAMPLE 4

A mixture of 3-oxotricyclo[2,2,1,0$^{2,6}$]heptane-5-anti-carboxylic acid and an excess of concentrated hydrochloric acid was heated for 1½ hours in an oil-bath at 120°C. On cooling the reaction mixture, 5-exo-chloro-2-oxobicyclo[2,2,1]-heptane-7-anti-carboxylic acid crystallised, was filtered off, washed with cold water and dried, to give material identical with that obtained by the process of Example 3.

EXAMPLE 5

A mixture of 3-oxotricyclo[2,2,1,0$^{2,6}$]heptane-5-anti-carboxylic acid (4.1 g.), glacial acetic acid (50 ml.) and 70% aqueous perchloric acid (1 ml.) was boiled under reflux for 6.25 hours. The resulting black mixture was cooled, poured into water (250 ml.) and extracted with ethyl acetate (130 ml., then 4 × 80 ml.). The extracts were combined, washed with water and dried, and the solvent was evaporated under reduced pressure. The residue was dissolved in sodium bicarbonate solution and extracted three times with ethyl acetate. The bicarbonate solution was acidified to pH 1 with dilute hydrochloric acid, saturated with salt and extracted 5 times with ethyl acetate. The extracts were combined, washed with brine and dried, and the solvent was evaporated to give a residue, which was crystallised from acetone/light petroleum to give 5-exo-acetoxy-2-oxobicyclo[2,2,1heptane-7-anti-carboxylic acid, m.p. 186°–187°C.

EXAMPLE 6

A 40% solution of peracetic acid (60 ml.) was added to a solution of 5-exo-bromo-2-oxobicyclo[2,2,1]heptane-7-anti-carboxylic acid (22.03 g.) in glacial acetic acid (220 ml.), and the mixture was stirred until thin layer chromatography (on silica, developed with benzene:ether:formic acid, 4:2:1) indicated the absence of the starting material (12 hrs.). A solution of sodium metabisulphite was then added, to destroy the excess of peracetic acid, and the mixture was diluted with water and extracted 6 times with ethyl acetate. The combined extracts were washed with water and dried, and the solvent was evaporated under reduced pressure. The residue was triturated with ether and cooled in a refrigerator to give 6-exo-bromo-3-oxo-2-oxabicyclo[3,2,1]octane-8-anti-carboxylic acid. A sample crystallised from a mixture of acetone and petroleum ether (b.p. 60°–80°C.) had melting point 178°–182°C. (decomposition).

EXAMPLE 7

The process described in Example 6 was repeated using 5-exo-chloro-2-oxobicyclo[2,2,1]heptane-7-anti-carboxylic acid in place of the 5-exo-bromo starting material, there is obtained 6-exo-chloro-3-oxo-2-oxabicyclo[3,2,1]octane-8-anti-carboxylic acid, m.p. 178.5°–182°C., after crystallisation from acetone light petroleum.

In a similar manner, using 2-oxobicyclo[2,2,1]heptane-7-anti-carboxylic acid in place of the 5-exo-bromo starting material, there is obtained 3-oxo-2-oxabicyclo[2,2,1]octane-8-anti-carboxylic acid, m.p. 130°–133°C., after crystallisation from acetone/light petroleum and sublimation under reduced pressure.

EXAMPLE 8

6-Exo-bromo-3-oxo-2-oxabicyclo[3,2,1]octane-8-anti-carboxylic acid (6.1 g.) and hydroxylamine hydrochloride (6.82 g.) were dissolved in 2,4,6-collidine (200 ml.), and the solution was stirred at room temperature for one-half hour and at 120°C. for 2 hours. The reaction mixture was cooled, acidified to pH 1 with 50% hydrochloric acid, and continuously extracted with ether for 48 hours. The extract was evaporated to dryness and triturated with a mixture of acetone and chloroform to give a crude solid which was filtered off and crystallised from acetone/light petroleum to give 2,3,3aβ,6aβ-tetrahydro-5α-hydroxy-2-oxocyclopenteno[b]furan-4β-carboxylic acid, m.p. 150°–152°C.

EXAMPLE 9

3α-Acetoxy-5β-bromo-2β-carboxycyclopent-1α-ylacetic acid (crude, from 4.58 g. of 6-exo-bromo-3-oxo-2-oxabicyclo-[3,2,1]octane-8-anti-carboxylic acid, see below) was dissolved in water and 8% sodium hydroxide solution was added, with cooling, to give pH 14. After 20 minutes at room temperature, the solution was acidified to pH 1 with dilute hydrochloric acid, and continuously extracted with ether for 48 hours. The ether extract was evaporated to dryness, and the residue was triturated with ether to give the cyclopentenofuran derivative, 2,3,3aβ,6aβ-tetrahydro-5α-hydroxy-2-oxo-cyclopenteno[b]furan-4β-carboxylic acid (single spot on thin layer chromatography). A sample was crystallised from a mixture of acetone and petroleum ether (b.p. 60°–80°C.) to give material of m.p. 150°–152°C.

The 3α-acetoxy-5β-bromo-2β-carboxycyclopent-1α-ylacetic acid used as starting material in the above process may be prepared as follows:

A solution of 6-exo-bromo-3-oxabicyclo[3,2,1]-octane-8-anti-carboxylic acid (4.58 g.) in glacial acetic acid (15 ml.) and 45% hydrogen bromide in acetic acid (35 ml.) was heated at 75°–80°C. for 2 hours. The solution was cooled and poured into water, and the mixture was extracted 5 times with ethyl acetate. The combined extracts were washed with water and dried, and the solvent was evaporated under reduced pressure to give the cyclopentane derivative, 3α-acetoxy-5β-bromo-2β-carboxycyclopent-1α-ylacetic acid as an oil.

EXAMPLE 10

2,3,3aβ,6aβ-Tetrahydro-5α-hydroxy-2-oxocyclopenteno[b]furan (739 mg.) was dissolved in water (10 ml.) containing 2 drops of phenolphthalein indicator, 5% sodium hydroxide solution was added until a permanent pink colouration was obtained, then a few mg. of the cyclopentenofuran derivative were added, to discharge the colour. A solution of freshly recrystallised p-bromophenacyl bromide (1.22 g.) in methanol was added, together with sufficient additional methanol to give a solution, and the mixture was heated under reflux for 1¼ hours. The reaction mixture was cooled, and the solid material which crystallised out was recrystallised from a mixture of methanol and chloroform to give 4-bromophenacyl 2,3,3aβ,6aβ-tetrahydro-5α-hydroxy-2-oxocyclopenteno[b]furan-4β-carboxylate, m.p. 158°–160°C. Further recrystallisation from acetone/petroleum ether raised the m.p. to 159°–160.5°C.

EXAMPLE 11

The product from Example 10 (344 mg.) 4-phenylbenzoyl chloride (365 mg.) in pyridine (6 ml.) was stirred at room temperature for 2.5 hours and poured into water, and the mixture was extracted 3 times with chloroform. The extracts were combined, washed with brine, and dried. The solvent was evaporated under reduced pressure, and the residue was crystallised first from chloroform/light petroleum and then from acetone/light petroleum, to give the 4-phenylbenzoate ester, 4-bromophenacyl 2,3,3a$\beta$,6a$\beta$-tetrahydro-2-oxo-5$\alpha$-(4-phenylbenzoyloxy)cyclopenteno[b]furan-4$\beta$-carboxylate, m.p. 161°–163°C.

EXAMPLE 12

The product from Example 11 (104 mg.) was dissolved in glacial acetic acid (10 ml.), zinc dust (0.96 g.) was added and the mixture was stirred at room temperature for 1¼ hours. The mixture was diluted with ether and filtered, and the filtrate was evaporated to dryness under reduced pressure. The residue was partitioned between sodium bicarbonate solution and ether, and the ether was discarded. The aqueous solution was washed twice with ether, acidified to pH 1 with dilute sulphuric acid, and extracted 4 times with methylene dichloride. The combined extracts were dried, and the solvent was evaporated to give a crystalline solid. Crystallisation from a mixture of ethyl acetate and petroleum ether (b.p. 60°–80°C.) gave the acid, 2,3,3a$\beta$,6a$\beta$-tetrahydro-2-oxo-5$\alpha$-(4-phenylbenzoyloxy)cyclopenteno[b]furan-4$\beta$-carboxylic acid, m.p. 174.5°–175.5°C.

EXAMPLE 13

The product from Example 8 or 9 (37 mg.) was dissolved in sulpholane (1 ml.) in an atmosphere of nitrogen. n-Butyllithium (0.28 ml. of a 1.43M solution in pentane) was added at room temperature, followed 15 minutes later by a solution of 4-phenylbenzoyl chloride (56 mg.) in sulpholane (0.5 ml.). The mixture was kept at room temperature for 1 hour, acidified with N hydrochloric acid and diluted with ethyl acetate (10 ml.). The organic phase was separated, washed with water and dried, and the solvent was evaporated under reduced pressure. The residue was purified by preparative thin layer chromatography on silica gel, developed with 3% acetic acid in ethyl acetate, $R_F = 0.5$. The $R_F$ and the n.m.r. spectrum were identical in all respects with the product obtained in Example 12.

EXAMPLE 14

A solution of methyl 5$\beta$-bromo-2$\beta$-methoxycarbonyl-3$\alpha$-(4-phenylbenzoyloxy)cyclopent-1$\alpha$ylacetate (126.5 mg.) in glacial acetic acid (5 ml.) with silver acetate (137 mg.) was heated at 90°C. for 1½ hours. The mixture was cooled and extracted with ethyl acetate. The extract was washed successively with water (twice), sodium bicarbonate solution and water, and was dried. The solvent was evaporated under reduced pressure, and the residue was crystallised from methanol to give methyl 2,3,3a$\beta$,6a$\beta$-tetrahydro-2-oxo-5$\alpha$-(4-phenylbenzoyloxy)cyclopenteno[b]furan-4$\beta$-carboxylate, m.p. 145°–146°C.

The methyl 5$\beta$-bromo-2$\beta$-methoxycarbonyl-3$\alpha$-(4-phenylbenzoyloxy)cyclopent-1$\alpha$-ylacetate used as starting material in the above process may be prepared as follows:

6-Exo-bromo-3-oxo-2-oxabicyclo[3,2,1]octane-8-anti-carboxylic acid (2.37 g.), methanol (20 ml.) and concentrated sulphuric acid (1 ml.) were mixed and kept at room temperature for 1 hour. The solution was neutralised with sodium bicarbonate, the methanol was evaporated under reduced pressure and the residue was extracted with ethyl acetate. The extract was washed with sodium bicarbonate (twice) and brine, and was dried, and the solvent was evaporated under reduced pressure, to give the hydroxy-ester, methyl 5$\beta$-bromo-3$\alpha$-hydroxy-2$\beta$-methoxycarbonylcyclopent-1$\alpha$-ylacetate, a liquid which decomposes on attempted distillation, and is used without purification in the following reaction.

A solution of the hydroxy-ester (473 mg.) and 4-phenylbenzoyl chloride (369 mg.) in pyridine (5 ml.) was kept at room temperature for 24 hours. A few drops of water were added, and the reaction mixture was poured into water and extracted with ethyl acetate (3 times). The extracts were combined, washed successively with dilute sulphuric acid (twice), sodium bicarbonate and saturated brine, and dried, and the ethyl acetate was evaporated under reduced pressure. The residue crystallised after trituration with methanol, and was recrystallised from carbon tetrachloride/light petroleum to give methyl 5$\beta$-bromo-2$\beta$-methoxycarbonyl-3$\alpha$-(4-phenylbenzoyloxy)cyclopent-1$\alpha$-ylacetate, m.p. 114°–115.5°C.

EXAMPLE 15

A solution of the product from Example 8 or 9 (366 mg.) in tetrahydrofuran (5 ml.) was cooled to 0°C. while diborane, generated from the addition of a solution of sodium borohydride (50 mg.) in diglyme to a stirred solution of boron trifluoride etherate in diglyme, is bubbled through in a stream of nitrogen. The tetrahydrofuran solution was kept at 0°C. for three-fourths hour, then water was added and the solution was extracted 6 times with ethyl acetate. The extracts were combined, washed successively with sodium bicarbonate solution and water, and dried. The solvents were evaporated under reduced pressure to give a residue which eventually solidified, to give 2,3,3a$\beta$,6a$\beta$-tetrahydro-4$\beta$-hydroxymethyl-2-oxo-5$\alpha$-(4-phenylbenzoyloxy)cyclopenteno[b]furan, m.p. 150°–152°C. after crystallisation from ethyl acetate, mixed m.p. with an authentic sample 149.5°–151.5°C.

EXAMPLE 16

2,3,3a$\beta$,6a$\beta$-Tetrahydro-2-oxo-5$\alpha$-(4-phenylbenzoyloxy)cyclopenteno[b]furan-4$\beta$-carbonyl chloride (39 mg.) was dissolved in toluene (2 ml.), 5% palladium on barium sulphate (20 mg.) was added, and the suspension was stirred under an atmosphere of hydrogen at room temperature for 4 hours. The catalyst was filtered off, the filtrate was diluted with ethyl acetate (3 ml.), washed with sodium bicarbonate and dried, and the solvent was evaporated under reduced pressure to give 2,3,3a$\beta$,6a$\beta$-tetrahydro-2-oxo-5$\alpha$-(4-phenylbenzoyloxy)cyclopenteno[b]furan-4$\beta$-carbaldehyde, $R_F = 0.2$ (20% ethyl acetate in methylene dichloride) identical by $R_F$ and n.m.r. spectroscopy with authentic material prepared by published methods.

The acid chloride used as starting material in the above process may be obtained by suspending 2,3,3a$\beta$,6a$\beta$-tetrahydro-2-oxo-5$\alpha$-(4-phenylbenzoyloxy)cyclopenteno[b]furan-4$\beta$-carboxylic acid (36 mg.) in toluene (2 ml.), at room temperature, containing oxalyl chloride (25.5 μl.). Dimethylformamide (2 drops) was added, the solution was stirred for 10 minutes at room temperature, and the mixture was evaporated to dryness under reduced pressure to give the crude acid chloride, which was used without purification.

EXAMPLE 17

A solution of 6-exo-chloro-8-anti-hydroxymethyl-3-oxo-2-oxabicyclo[3,2,1]octane (1.135 g.) in dry methylene dichloride (5 ml.) was added to a solution of chromium trioxide (3.575 g.) in pyridine (5.744 ml.) and methylene dichloride (100 ml.). The mixture was stirred for 15 minutes at room temperature, and the solution was decanted from a tarry residue. The residue was washed with ether, which was combined with the decanted solution, and diluted with ethyl acetate. The solution was washed successively with N hydrochloric acid, sodium bicarbonate solution and brine, and was dried. The solvent was evaporated under reduced pressure, and the residue crystallised on trituration with ether, to give 6-exo-chloro-3-oxo-2-oxabicyclo[3,2,1]octane-8-anti-carbaldehyde, n.m.r. in deuteriochloroform (δ values):

2.4-3.3, 6H, multiplet, C-1, 4, 7 and 8 protons
4.37, 1H, broad singlet, C-6 proton
5.25, 1H, broad singlet, C-1 proton
9.8, 1H, singlet, —CHO

EXAMPLE 18

Sodium hydride (50% dispersion in oil, 29 mg.) was added to a solution of dimethyl 2-oxoheptylphosphonate (169 mg.) in dry 1,2-dimethoxyethane (2 ml.), and the mixture was stirred and cooled to −60°C. A solution of the product from Example 17 (57 mg.) in dry 1,2-dimethoxyethane (2 ml.) was added in one portion, and the mixture was allowed to warm to room temperature, diluted with ethyl acetate, washed successively with water, sodium bicarbonate solution and brine, and dried. The solvent was evaporated under reduced pressure, and the residue was purified by chromatography on silica, eluting with ether, to give 6-exo-chloro-3-oxo-8-anti-(3-oxo-oct-1-trans-enyl)-2-oxabicyclo[3,2,1]octane, m.p. 65°-67°C., after crystallisation from benzene/light petroleum.

EXAMPLE 19

A solution of the product from Example 18 (279 mg.) in ethanol (15 ml.) was stirred and cooled to −20°C., and sodium borohydride (124.5 mg.) was added in one portion. The mixture was stirred at −20° to −25°C. for 2 hours, the excess hydride was decomposed by addition of water, and extracted with ethyl acetate. The extract was washed with saturated brine and dried, and the solvent was evaporated under reduced pressure to give 6-exo-chloro-8-anti-(3-hydroxyoct-1-trans-enyl)-2-oxabicyclo[3,2,1]octane as a colourless oil, n.m.r. in deuteriochloroform (δ values):

0.9, 3H, triplet  ⎫
1.1-1.8, 8H, multiplet ⎬ n-pentyl protons
1.9, 1H, broad singlet, OH
2.2-3.1, 6H, multiplet, C-4, 5, 7 and 8 protons
4.1, 1H, multiplet, —CH(OH)—
4.3, 1H, multiplet, —CHCl—
4.84, 1H, broad singlet, —CH.O.CO—
5.8, 2H, triplet, —CH=CH—

EXAMPLE 20

To a solution of the product from Example 19 (101 mg.) in tetrahydrofuran (3 ml.) was added a solution of sodium hydroxide (22 mg.) in water (2.5 ml.) and 100 volume hydrogen peroxide (0.75 ml.). The mixture was kept at room temperature for 1.25 hours, poured into sodium metabisulphite solution, acidified, and extracted with ethyl acetate (4 times). The extracts were combined, washed with saturated brine and dried, and the solvent was evaporated under reduced pressure to give 2,3,3aβ,6aβ-tetrahydro-5α-hydroxy-4β-(3-hydroxyoct-1-trans-enyl)-2-oxocyclopenteno[b]furan, identical by thin-layer chromatography and n.m.r. spectroscopy with authentic material prepared by published methods.

EXAMPLE 21

The product from Example 19 (100 mg.), hydroxylamine hydrochloride (121 mg.) and anhydrous sodium acetate (143 mg.) were dissolved in a mixture of water (4 ml.) and isopropanol. The solution was stirred at room temperature for 1 hour, then heated under reflux for 12 hours. The solution was cooled, acidified to pH 1 with dilute hydrochloric acid, diluted with water and extracted 4 times with ethyl acetate. The extracts were combined, washed with saturated brine and dried, and the solvent was evaporated under reduced pressure. Thin layer chromatography shows the residue to consist of unchanged starting material, 2,3,3aβ,6aβ-tetrahydro-5α-hydroxy-4β-(3-hydroxyoct-1-trans-enyl)-2-oxocyclopenteno[b]furan identical by $R_F$ with authentic material, and one other compound.

What we claim is:

1. A lactone of the formula:-

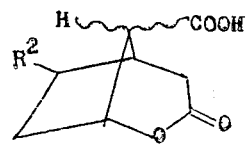

wherein $R^2$ is hydrogen, bromine, chlorine, iodine or alkanoyloxy of 1 to 6 carbon atoms.

2. The lactone of claim 1 which is 6-exo-bromo-3-oxo-2-oxabicyclo(3,2,1)octane-8-anti-carboxylic acid.

3. The lactone of claim 1 which is 6-exo-bromo-3-oxo-2-oxabicyclo(3,2,1)octane-8-anti-carboxylic acid.

* * * * *